United States Patent [19]

Bergamini et al.

[11] Patent Number: 5,679,665
[45] Date of Patent: Oct. 21, 1997

[54] PHARMACEUTICAL FORMULATION COMPRISED OF POLYMYXINTRIMETHOPRIM AND AN ANTI-INFLAMMATORY DRUG FOR OPHTHALMIC AND OTIC TOPICAL USE

[75] Inventors: Michael Van Wie Bergamini; Teresa Borras Sanjurjo, both of El Masnou; Jordi Coll Colomer, Barcelona; Ricardo Notivol Paino, Barcelona; Carmen Oros Laguens, Barcelona; Jose Alberto Vallet Mas, Barcelona, all of Spain

[73] Assignee: Laboratorios Cusi, S.A., El Masnou, Spain

[21] Appl. No.: 549,556

[22] Filed: Oct. 27, 1995

Related U.S. Application Data

[63] Continuation of Ser. No. 132,362, Oct. 6, 1993, abandoned.

[30] Foreign Application Priority Data

Oct. 7, 1992 [ES] Spain ........................... 9201979

[51] Int. Cl.$^6$ .................. A61K 31/56; A61K 31/505; A61K 31/21
[52] U.S. Cl. .................. 514/171; 514/272; 514/515; 514/912
[58] Field of Search ............... 514/171, 272, 514/515, 912

[56] References Cited

FOREIGN PATENT DOCUMENTS 0 037 043 10/1981 European Pat. Off. .

OTHER PUBLICATIONS

"Trimethoprim–polymyxin Ophthalmic Solution Versus Chloramphenicol Ophthalmic Solution In The Treatment Of Bacterial Conjunctivitis" –(Pharmakatherqapeutika, vol. 3, No. 4, 1982).
"Efficacy Of Various Drug Regimens In Benighn Otorrhea' — Current Therapeutic Research", vol. 37, No. 6, 1985.
Chemical Abstract 96 (4) 24803 X (1981). Hugh et al.
Biosis Abstract of Vet Med Nauki, 22 (7). 1985, pp. 40–47. Verheijden et al.

*Primary Examiner*—Zohreh Fay
*Attorney, Agent, or Firm*—Darby & Darby

[57] ABSTRACT

It comprises: 0.005–1.0% of trimethoprim or a pharmaceutically acceptable salt thereof: 0.01–0.3% of polymyxin or a pharmaceutically acceptable salt thereof: 0.001–5% of a steroidal or non-steroidal anti-inflammatory drug and, optionally, one or more ingredients selected from among isotonizing agents, pH buffers, viscosity modifying agents, wetting agents, chelating agents, anti-oxidants, preservatives and vehicles. The formulation has a pH between 4 and 8.5.

It is applicable in the treatment of ophthalmic and otic infections accompanied by inflammation.

20 Claims, No Drawings

PHARMACEUTICAL FORMULATION COMPRISED OF POLYMYXINTRIMETHOPRIM AND AN ANTI-INFLAMMATORY DRUG FOR OPHTHALMIC AND OTIC TOPICAL USE

This is a continuation of application Ser. No. 8/132,362, filed Oct. 6, 1993, now abandoned.

TECHNICAL FIELD OF THE INVENTION

The present invention fits within the technical field of pharmaceutical formulations used to treat infectious processes accompanied by inflammation of the eyes, the surrounding area thereof as well as of ears.

Specifically, the present invention provides a formulation comprised of polymyxin, trimethoprim and an anti-inflammatory drug for ophthalmic and otic topical use.

PRIOR ART

Formulations used to treat ophthalmic and/or otic infections, whether or not they are accompanied by a concomitant inflammatory process, have been known for quite some time, though, the development of new compositions that are equally effective or more effective than known ones with less side effects and which are easier to administer, as well as which are stabler during storage, among other advantages, is still necessary.

U.S. Pat. No. 3,985,873 of 12 Oct. 1976, describes an ophthalmic solution suitable to treat microbial infections, especially, bacterial infections of eyes and the surrounding area thereof, containing sulfacetimide, a medicinal or pharmaceutically water soluble salt of polymyxin, especially polymyxin B, and water, the solution having a pH between 4.5 and 6.5. This solution is especiaoly applicable to eye infections, such as acute or chronic conjunctivitis, infected sockets, ulcers of the cornea, keratitis, episcleritis, blepharitis, etc., also being applicable in eye surgery or in the case of serious eye damage.

PCT W.O. 89/0957 of 9 Mar. 1989 describes pharmaceutical compositions that comprise tobramycin and a steroid such as dexamethasone or fluorometholone for ophthalmic topical use. These compositions are especially applicable in treating patients with symptoms related to ophthalmic bacterial infections which involve inflammation as well as in treating patients that may be predisposed to develop an ophthalmic infection, as a result of an immunosuppressor effect attributible to the steroid component of the composition or as a result of a situation no related to steroid therapy.

Canadian patent no. 2,013,188 of 27 Mar. 1990 refers to a preservative system for antimijcrobially effective ophthalmic formulations. Said formulations include a non-steroidal anti-inflammatory drug containing a —COOH group in combination with an antibiotic, the preservative system being formed by a quaternary ammonium preservative and a non-ionic polyoxyethylated octyl phenol surface active agent, and all in an aqueous medium. These formulations are useful for treating diseases and/or situations that are caused by, associated with, or accompanied by inflammatory processes. Among others, glaucoma, macular edema, uveitis, diabetic retinopathy or conjunctivitis can be mentioned, or in the cause of any traumatism due to surgery or any eye injury.

On the other hand, it is known that the trimethoprimpolymyxin B association, in the preparation of collyria for ophthalmic use, has been shown to be highly effective in treating bacterial conjunctivitis caused by diverse agents (Lamberts, D. V., Buka, T; Knowlton, G. M. Clinical evaluation of trimethoprim-containing ophthalmic solutions in humans. Am. J. Ophthalmol. 1984, 98: 11–16; and Nozik, R. A.; Smolin, G.; Knowlton, G.; Austin, R. Trimethoprim-Polymyxin B ophthalmic solution in treatment of surface ocular bacterial infections. Ann. Ophthalmol. 1985, 17: 746–748) among which Neisseria gonorrheae must be excepted. Different researchers have shown that the association of both drugs is synergic against different bacterial species.

Trimethoprim is active "in vitro" against Haemofilus, *Escherichia coli, Klebsiella pneumoniae,* Moraxella, Enterobacter aerogenes, Proteus, Salmonella and Shigella. Pseudomonas are not susceptible at all or very slightly.

Polymyxin B has a bacterial action on different gram negative bacteria, such as: Escherichia, Heamophilus, Klebsiella, Pasteurella, Salmonella, Shigella, Vibrio and *Pseudomona aeruginosa,* the action thereof on the last one being the main reason why the association for ophthalmic use has been made.

Likewise, the applicant itself (internal documentation of Laboratorios Cusi, S. A. Double blind clinical test between the association of trimethoprim-polymyxin B-dexamethasone and the association of gentamycin in otitis externa. 1990) has also successfully used this association to treat diffuse otitis externa as is shown in the double blind clinical test with 100 patients, unpublished, in which the trimethoprim-polymyxin preparation was shown to be highly effective, just like gentamycin-dexamethasone, in clinical and bacteriological healing of these processes.

Likewise, it is known that the association of a corticosteroid with an antibiotic for the treatment of infectious processes of the anterior eye pole and of the external ear, have the following advantages:

1. They shorten the evolution of the disease since the signs and symptoms disappear more rapidly.

2. The combination in a single container of the antibiotic and the corticosteroid makes treating the patient easier, avoiding mistakes and improving the following of the same.

3. Corticosteroids administered together with antibiotics, both in topical form, reduce itching and irritation of the mucous membrane that the antibiotics after administration thereof (tolerance.)

The advantages, effectiveness and safety of the preparations with antibiotic and corticosteroid combinations for treating infectious processes of the anterior pole and ears, has been repeatedly proven in numerous clinical tests and experimental studies.

Topical corticosteroids can on occasions cause undesirable effects, however, when they are correctly used in combination with suitable antibiotics, they are very useful for treating pathologies in which infectious agents take part. These combinated preparations are a strong therapeutic means for ophthamologists as well as general practitioners A double blind study carried out by Aragones (Aragones, J. V. The treatment of blepharitis: a controlled double blind study of combination therapy. Annals of Ophthalmology 1973. January 49–52) in patients with chronic blepharitis, showed that the combination of an anti-inflammatory drug and an anti-infectious drug is much more effective than treatment with only an anti-infectious drug. The patients treatly only with an antibiotic and whose symptoms persisted were treated with corticosteroids, experimenting a spectacular improvement. No undesirable effects due to the corticosteroids were found. The author emphasizes the advantages of a single container for administering the treatment when two drugs should be administered since this prevents confusion and the patient's correct following of the treatment.

Clinical studies done on blepharitis and blepharoconjunctivitis show that the antibiotic-corticosteroid combination alleviates more rapidly the signs and symptoms and is effective in more serious varieties of blepharitis. They are of the opinion that these associations should be available to specialists at least in the cases of staphylococcic blepharoconjunctivitis and blepharitis of a mixed etiology. (Lepold, L H. Clinical use of Corticosteroids in anterior segment inflammatory disease initiated by replica ting agents. Tr. Am. Acad. Ophth. § Otol. (1975), 79 (January–February): 117–127.) Alexander et al. A new corticosteroid-antibiotic preparation in eye and ear infections. General Practitioner Clinical Trials (1966); 197: 94–96 obtains similar conclusions in bacterial blepharoconjunctivitis as well as otitis externa and otitis media.

In a study carried out on an experimental model of bacterial keratitis in rabbits (Liebowitz, H. M.; Kupferman, A. Topically administered corticosteroids. Arch. Ophthalmol. (1980), 98: 1287–1290) the effects produced by the interaction of an antibiotic and a corticosteroid were verified. The results showed that despite the believed interference that corticosteroids can have on the host's defense mechanisms against the infection, the balance of the combination of the same administered topically together with an antibiotic, is positive. The corticosteroid has an unspecific anti-inflammatory action and the antibiotic continues to eliminate microorganisms without apparent interference. The conclusion is reached that a corticosteroid administered topically together with a topical suitable antibiotic does not increase bacterial replication if the corticosteroid is not administered more frequently than the antibiotic. When both drugs are combined in the same preparation, they are administered simultaneously and with the same frequency.

Leibowitz and Kupferman (Leibowitz, H. M.; Kupferman, A. Drug interaction in the eye, Arch. Ophthalmol. (1977), 95: 682–685) did an experimental study for the purpose of studying the possible interactions between the corticosteroid and the antibiotic upon being instilled together in the eye. None of the combinations studied showed a reduction of the effectiveness in comparison with the corticosteroid alone and greater effectiveness that seems to indicate the synergic effect between both compounds was even observed.

There are also references to the use of corticosteroids in the course of treatment of eye infections with antibiotics (Manabe, R.; Murai, Y. Clinical use of sulbenicillin eye drops. Folia Ophthal. Jap. (1974) 25 (12): 1313–1318), both topically, for the purpose of reducing itching and irritation caused by antibiotics.

Despite all that which has been said above, present eye anti-infectious therapy still has quite a number of inconveniences, some of which are indicated hereinafter:

Treatment of eye infections with trimethoprim in an ophthalmic solution is effective against gram positive germs (S. aureus, S. epidermidis, H. influenzae, Strp. pneumoniae and Strp. viridans ) and some gram negative germs (E. coli, Klebsiella pneumoniae, Proteus mirabilis), but its action spectrum is incomplete.

Polymyxin B is only active against gram negative microorganisms (Enterobacter, E. coli, Klebsiella and many strains of Pseudomona aeruginosa), but its action spectrum is also incomplete.

Another antibiotics of ophthalmic use such as gentamycin, ampicillin, tobramycin and cephalosporins are very frequently resistant to certain microorganisms, thus use thereof is being limited little by little. The use of said antibiotic combination improves the possibilities of treating these cases.

Besides, reactions of hypersensitivity to the above cited antibiotics may take place. In the case of tobramycin the frequency of such a reaction is up to 3%.

Other broad spectrum antibiotics such as Cloramphenicol can be the cause of serious adverse reactions (aplastic anemia) even when used topically.

Likewise, there are problems of tolerance for most topical antibiotics, since even when they are effective, a formulation that does not produce irritation has not been achieved.

Therefore, a broad spectrum product, that is effective against gram positive and gram negative germs, including Pseudomona aeruginosa, is necessary. Therapeutics should be safe, having the lowest frequency possible of adverse local and systemic reactions, as well as of allergic reactions.

Besides, infectious processes are very frequently accompanied with a significant inflammatory component which has to be treated with a non-steroidal anti-inflammatory drug (NSAID) or with topical corticosteroids. Although these are highly effective they are not devoid of undesirable side effects such as a worsening of the infectious process and an increase of intra-ocular pressure. When the NSAID or the corticosteroid is administered together with a suitable antibiotic and not more frequently than the latter, these adverse reactions are reduced to the minimum.

Therefore, it would be very advantageous to have a single preparation that would alleviate the infectious process as well as the inflammation that accompanies it. This would mean greater ease for the doctor and for the patient and would improve the degree in which the treatment is followed. The antibiotic-corticosteroid combination, although, essential, does not cover, as it has already been indicated, the entire spectrum of clinical possibilities since in certain patients the administration thereof is contraindicated. In these cases a non-steroidal anti-inflammatory drug (NSAID) could be used without any risks and with a similar anti-inflammatory effect.

The present invention provides formulations applicable to treat ophthalmic and otic infections accompanied by inflammation that have, among others, the following advantages:

Association in a single preparation of an antibiotic and an anti-inflammatory drug, where the action spectrum of the antibiotic is similar to that of cloramphenicol, but without having its side effects.

Use, in the formulation, of a steroidal or a non-steroidal anti-inflammatory drug (NSAID) indistinctly, or a mixture of both.

Choice of an optimal combination of vehicles that makes it possible to attain some stable, well tolerated and therapeutically effective preparations.

DETAILED DESCRIPTION OF THE INVENTION

The present invention refers to a pharmaceutical formulation in which two antibiotics and one anti-inflammatory drug are combined for topical use thereof in infectious eye and ear processes that are accompanied by inflammation.

In particular the invention refers to the combination of 2,4-diamino-5-(3',4',5'-trimethoxybenzyl) pyrimidine, known as trimethoprim, polyxymyxin, preferably polymyxin B and a steroidal anti-inflammatory drug, preferably dexamethasone or clobetasone, or a non-steroidal anti-inflammatory drug, preferably diclofenac or indomethacin, or a mixture of both types of anti-inflammatory drugs.

Infectious eye processes accompanied by inflammation that can be treated with the formulations described in the present invention are glaucoma, uveitis, diabetic retinopathy, conjunctivitis or any eye trauma caused by an accident or surgery. Besides, eye infections can also be treated with the formulations described in the present invention.

Likewise, with the formulations described in the present invention, infectious ear processes accompanied by inflammation, such as for example, otitis externa, can can be treated. Besides, ear infections can be treated with the formulations described in the present invention.

Trimethoprim of structural formula (I):

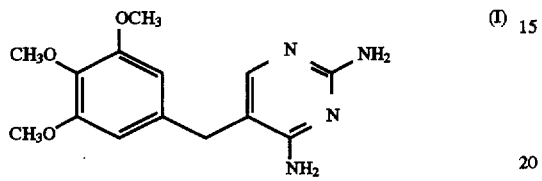
(I)

is an antibacterial drug active against gram positive microorganisms (*S. aureus, S. epidermidis,* H. influenzae, *Strep. pneumoniae* and *Strep. viridans*) and gram negative microorganisms (*E. coli, Klebsiella pneumoniae, Proteus mirabills.*) The present invention also includes pharmaceutically acceptable salts of said compound.

Within the substances that can be considered as pharmaceutically suitable to form soluble salts of trimethoprim, mineral acids (sulfuric acid, phosphoric acid, hydrochloric acid, hydrobromic acid, iodohydric acid) and organic acids of between 1 to 20 carbon atoms, preferably those of 1 to 10 carbon atoms (tartaric acid, citric acid, lactic acid, acetic acid, ethylenediaminetetraacetic acid.) Soluble salts of trimethoprim are formed by reaction of trimethoprim with the corresponding acid.

A group of cationic peptide compounds is known as polymyxin, of which specifically polymyxin B stands out. Polymyxin B is a mixture of polymyxin $B_1$ and polymyxin $B_2$ of structural formula (II):

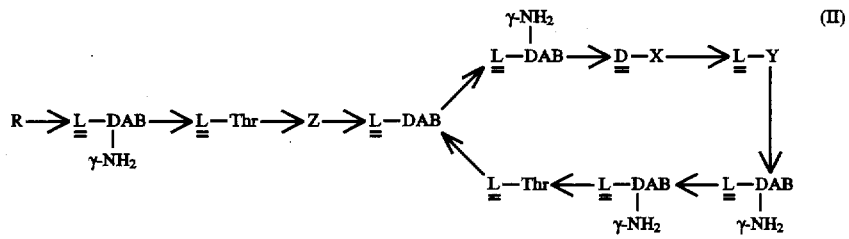
(II)

(Polymyxin $B_1$: R=(+)-6-methyloctanoyl; X=phenylalanine; Y=leucine; Z=L-DAB.

Polymyxin $B_2$: R=(+)-6-methylheptanoyl; X=phenylalanine; Y=leucine: Z=L-DAB.

DAB: α,α-diaminobutyric acid)

Polymyxin is active against different gram negative organisms (Enterobacter, *E. coli,* Klebsiella and many strains of *Pseudomonas aeruginosa.*) The present invention also includes pharmaceutically acceptable salts of said compounds.

The present invention is not restricted to a polymyxin in particular and all polymyxins described on pages 1205 and 1206 of the Merck Index, 11th. edition are considered to be included, though for the effects of the present invention polymyxin B is the compound that is considered to be the most suitable. For the effects of the present invention polymyxin is used as a pharmaceutically acceptable water soluble salt. In this way, it can be dissolved in water without stirring, though stirring can be used to speed up the dissolving process. The pharmaceutically acceptable salts used the most are sulfate or chlorohydrate.

The combination of trimethoprim with polymyxin B improves and broadens the microbiological activity against gram negative microorganisms (*E. coli,* Klebsiella, H. influenzae, Salmonella, Pasteurella, Bordetella, Shigella and in particular *Pseudomonas aeruginosa.*) In this way, a microbiological spectrum similar to that of Cloramphenicol but without its side effects is attained.

The formulations of the present invention include an anti-inflammatory drug. Said anti-inflammatory drug can be a steroidal type drug, such as, dexamethasone of structural formula (III):

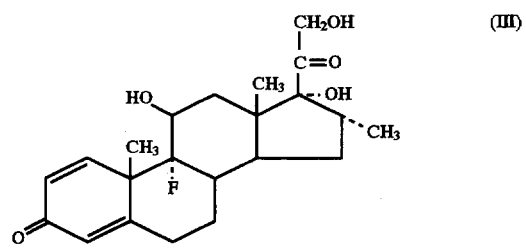
(III)

Clobetasone, of structural formula (IV):

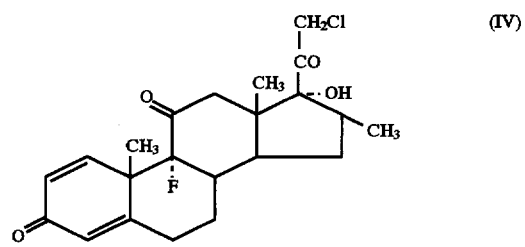
(IV)

Medrisone, of structural formula (V):

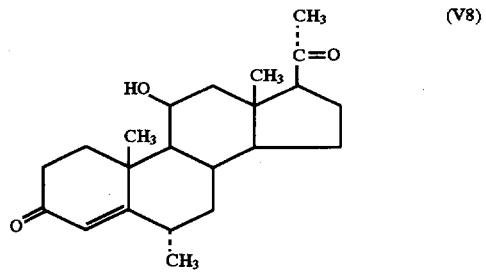
(V8)

Fluorometholone, of structural formula (VI):

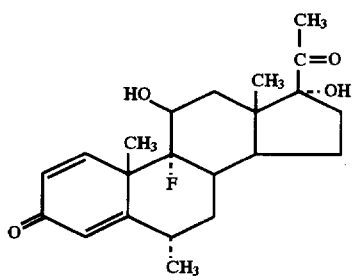

or else a non-steroidal type drug, such as sodium diclofenac of structural formula (VII):

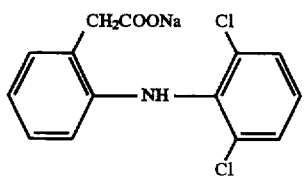

Indomethacin, of structural formula (VIII)

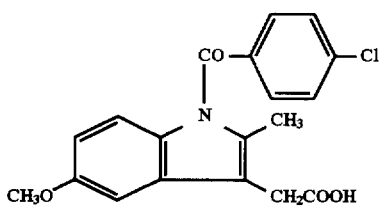

Flurbiprofen, of structural formula (IX)

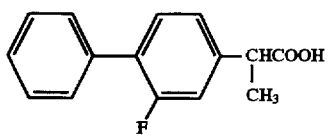

or Suprofen, of structural formula (X):

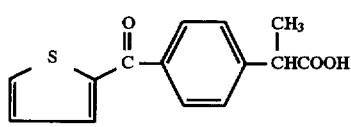

or Pranoprofen, of formula (XI):

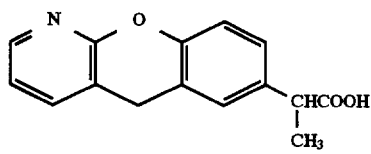

or Kerotolac of formula (XII):

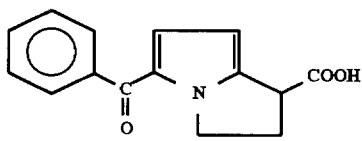

or else a combination of both types of anti-inflammatory drugs. The present invention also includes pharmaceutically acceptable isomers, esters and salts of the cited compounds.

The compositions of the present invention comprise the combination of polymyxin, trimethoprim and an anti-inflammatory drug. The compositions also include others compounds traditionally used in ophthalmic and otic preparations, such as isotonizing agents, pH buffers, viscosity modifying agents, wetting agents, chelating agents, antioxidants and preservatives.

In the following paragraphs, of the descriptive part of the present specification as well as of the set of claims, the percentages are expressed as weight/volume in those cases in which the resulting pharmaceutical form is a solution, suspension, emulsion or liquid fraction of an extemporaneous preparation. However, in the cases in which the resulting product of the application of the invention is an ointment or solid fraction of an extemporaneous preparation, the percentage is expressed as weight/weight.

Sodium chloride, glycerol, mannitol and sorbitol, among others, can be cited as isotonizing agents. These compounds are used to achieve the required tonicity in the preparation. These compounds are typically used at levels between 0.7 and 1.4%.

Citrates, borates and phosphates, among others, can be included as pH buffers. This type of product is introduced in the formulations to keep the pH stable for the life of the product and to improve tolerance thereof when the use of the product requires this. These compounds are typically used at levels between 0.01 and 2.0%.

As viscosity modifying agents, that improve the time during which the product remains where it has been administered or they ensure the homogeneity of the dosage in the cases in which the resulting product is a suspension, polyvinyl alcohol, polyvinylpyrrolidone, metylcellulose, hydroxypropylcellulose, hydroxyethylcellulose, carboxymethylcellulose, hydroxypropylmethylcellulose, among others, can be cited. These compounds are typically used at levels between 0.01 and 2.0%.

As wetting agents, that improve the contact between the solid and the aqueous vehicle in the compounds that result to be suspensions or that improve the solubility of some of the components in the formulation, polyethoxylated fatty alcohols, polyethoxylated alkylphenols, polyethoxylated fatty acids, sorbitan esters, alkanolamides, among others non-ionic surface active agents, can be included. These compounds are typically used at levels between 0.01 and 2.0%.

As chelating agents we can cite citric acid and disodium salt of ethylenediaminetetraacetic acid, EDTA. These compounds are included to improve the action of the preservatives. These compounds are typically used at levels between 0.01 and 2.0%.

As antioxidants to stabilize the formulations included in the present invention, we can point out ascorbic acid and sodium methabisulfate, among others. These compounds are typically used at levels between 0.01 and 2.0%.

As preservatives, to prevent contamination of the product, quaternary ammonium derivatives, such as benzalkonium chloride, cetylmethylammonium bromide, cetylpyridine chloride, organomercurial derivatives, such as thimerosal, phenylmercuric acetate and phenylmercuric phenyl and methyl and propyl p-Hydroxybenzoates, and the sodium salts thereof, chlorbutanol, beta-phenylethyl alcohol, benzyl alcohol, chlorhexidine diacetate, digluconate, among others, can be included. The formulations of the present invention also include mixtures of the cited compounds. These compounds are typically used at some levels between 0.001 and 1.0%.

Other optional vehicles can be used in terms of the characteristics of the steroids used, such as can be agents which increase stability (cyclodextrins), cryoprotective agents (dextrane, mannitol, citric acid, tartaric acid) when the resulting pharmaceutical form has to be an extemporaneous preparation to improve the stability, solvents typically used in otic preparations (ethanol, glycerol, propilenglycol, etc.) or vehicles normally used in pharmaceutical ointments (mineral oil, paraffin, lanolin, cholesterol, etc.)

The present invention includes the different pharmaceutical forms (solutions, suspensions, emulsions, ointments and extemporaneous preparations) obtained upon combining the different above mentioned compounds. The characteristics of the compounds chosen can condition the pharmaceutical form necessary to obtain a stable, well tolerated and therapeutically effective preparation.

In accordance with the present invention, the resulting combination includes between 0.005 and 1.0% of trimethoprim (as a base), preferably between 0.010 and 0.5% trimethoprim (as a base), between 0.01 and 0.3% of polymyxin (as a base), preferably between 0.5 and 0.15% polymyxin (as a base), and between 0.001 and 5% of the respective anti-inflammatory drugs, preferably between 0.05 and 3% of the anti-inflammatory drugs.

In practice, the amounts of polymyxin included in the present invention vary between 200,000 and 2,000,000 international units per 100 ml., the values between 400,000 and 1,600,000 being the preferred ones.

The pH of the formulations included in the present invention vary between 4 and 8.5, depending on the optimal rrange of the anti-inflammatory drugs, or mixture thereof, chosen. In order to adjust the pH of the formulations to the desired value, aside from the above mentioned buffers, acids (hydrochloric acid, sulfuric acid, etc.) or bases (sodium hydroxide, potassium hydroxide, etc.) can be used.

The amount of preparation that can be administered to the receptor animal depends on the nature of the animal (species, age, size), as well as the general state of health and seriousness and type of disease suffered from. Although the dosage is to be established by the doctor, it is recommended that the formulations included in the present invention be administered 2 to 4 times a day, instilling one or two drops each time.

The formulations included in the present invention can be packaged in the containers normally used for this type of preparation, in accordance with the resulting pharmaceutical form.

In the cases in which the use thereof so requires, the combinations included in the present invention have to be made under sterile conditions.

The presence of polymyxin and of trimethoprim does not affect the activity of the anti-inflammatory drugs used, as well as the presence of the anti-inflammatory drugs does not interfere in the antimicrobial activity of the mixture of polymyxin and trimethoprim against *Pseudomonas aeruginosa* and *Staplylococcus aureus*.

The formulations described in the present invention turn out to be antimicrobiologically effective according to the criteria of the British Pharmacopoeia against *Pseudomonas aeruginosa, Staphyococcus aureus, Candida albicans* and *Aspergillus niger.*

After 24 months of storage at room temperature it has been observed that the physical, physicochemical, chemical, microbiological and therapeutic characteristics of the formulations included in the present invention are maintained.

EMBODIMENTS OF THE INVENTION

The present invention is additionally illustrated by means of the following examples representative of the compositions included in the present invention, which should not be considered as restrictions of the scope of the same.

EXAMPLE No 1

Ophthalmic Suspension

| SUBSTANCE | AMOUNT PER 100 ml. |
|---|---|
| Trimethoprim base | 0.100 g. |
| Polymyxin B sulfate | 1,000,000 I.U. |
| Clobetasone 17 Butyrate | 0.100 g. |
| Hydroxyproylmethylcellulose | 0.500 g. |
| Sodium chloride q.s. | 300 mOsol/kg. |
| Polysorbate 80 | 0.100 g. |
| Sodium methyl p-hydroxybenzoate | 0.035 g. |
| Sodium propyl p-hydroxybenzoate | 0.023 g. |
| Sulfuric acid 25% | 1.2 ml. |
| Sodium hydroxide 40% q.s. | pH 5.2–5.8 |
| Purified water q.s. | 100 ml. |

In order to obtain the ophthalmic solution 90% of the water of the formulation is put in a suitable container and sulfuric acid and trimethoprim are added. The pH is adjusted with sodium hydroxide and the following components are added: sodium methyl p-hydroxybenzoate, sodium propyl p-hydroxybenzoate, sodium chloride, Polysorbate 80 and hydroxypropylmethylcellulose. The volume is completed with purified water and the resulting solution is filtered through a previously sterilized 0.22 micra filtration system. The resulting filtrate is collected in a sterile area and under these conditions previously sterilized Clobetasone 17 butyrate is added. The system is homogenized with a rotary agitator. The suspension obtained is dosed in previously sterilized suitable containers.

EXAMPLE No 2

Extemporaneous Solution

Fraction: Lyophile

| Substance | Amount per 100 ml. |
|---|---|
| Fraction: Lyophile | |
| Sodium dexamethasone phosphate equivalent to dexamethasone base | 0.100 g. |
| Trisodium citrate | 2.500 g. |
| Polysorbate 80 | 0.100 g. |
| Citric acid q.s. | pH 7.6–8.0 |
| Fraction: Active solvent | |
| Trimethoprim base | 0.100 g. |
| Polymyxin B sulfate | 1,000,000 I.U. |
| Hydroxyproylmethylcellulose | 0.500 g. |
| Sodium chloride q.s. | 300 mOsmol/kg. |
| Benzalkonium chloride | 0.010 g. |
| Sulfuric acid 25% | 1.2 ml. |
| Sodium hydroxide 40% q.s. | pH 5.5–5.9 |
| Purified water q.s. | 100 ml. |

In order to obtain the fraction corresponding to the lyophile sodium dexamethasone phosphate, trisodium citrate and Polysorbate 80 are dissolved in the necessary amount of purified water. The pH is adjusted with citric acid and the volume is completed with purified water. The resulting solution is filtered through a previously sterilized 0.22 micra filtration system. The resulting filtrate is dosed in previously steilized vials and is subjected to a lyophilization process. Once said operation has been completed, the vials are sealed with previously sterilized stoppers.

In order to obtain the fraction corresponding to the active solvent 90% of the water of the formulation is put in a suitable container and sulfuric acid and trimethoprim are added. The pH is adjusted with sodium hydroxide and benzalkonium chloride and sodium chloride are added. The volume is compelted with purified water and the resulting solution is filtered through a previously sterilized 0.22 micra filtration system. The resulting filtrate is collected in a sterile area and is dosed in previously sterilized suitable containers.

EXAMPLE No 3

Ophthalmic Solution

| SUBSTANCE | AMOUNT PER 100 ml. |
|---|---|
| Trimethoprim base | 0.100 g. |
| Polymyxin B sulfate | 1,000,000 I.U. |
| Sodium diclofenac | 0.100 g. |
| Sodium chloride q.s. | 300 mOsol/kg. |
| Polysorbate 80 | 0.100 g. |
| Benzalkonium chloride | 0.010 g. |
| EDTA Na$_2$ | 0.100 g. |
| Sulfuric acid 25% | 1.2 ml. |
| Sodium hydroxide 40% q.s. | pH 6.2–6.8 |
| Purified water q.s. | 100 ml. |

In order to obtain the ophthalmic solution 90% of the water of the formulation is put in a suitable container and sulfuric acid and trimethoprim are added. The pH is adjusted with sodium hydroxide and the following components are added: benzalkonium chloride, sodium chloride, Polysorbate 80, EDTA Na$_2$ and sodium diclofenac. The volume is completed with purified water and the resulting solution is filtered through a previously sterilized 0.22 micra filtration system. The resulting filtrate is dosed in previously sterilized suitable containers.

EXAMPLE No 4

Ophthalmic ointment

| SUBSTANCE | AMOUNT PER 100 g. |
|---|---|
| Trimethoprim base | 0.100 g. |
| Polymyxin B sulfate | 1,000,000 I.U. |
| Medrisone | 1,000 g. |
| Paraffin q.s. | 100 g. |

In order to obtain the ophthalmic ointment, each one of the previously sterilized active principles is separately mixed with an amount of paraffin 50 times greater than the weight thereof. Each one of the mixtures is separately refined in a roll grinder and subsequently they are mixed with the remaining amount of paraffin. The mixture is homogenized in a beater, it is refined again in a roll grinder if necessary and finally it is dosed in previously sterilized tubes.

Preclinical Tests

In the following paragraphs the term Ophthalmotrim designates the combination of trimethoprim and polymyxin B sulfate.

A-Microbiology

The preservative effectiveness (PET/Challenge Test) corresponding to the beginning of the study of the stability of the ophthalmic specialties Ophthalmotrim-Dexamethasone and Ophthalmotrim-Clobetasone and of the otic specialty Ophthalmotrim-Dexamethasone has been determined. The two ophthalmic specialties have benzalkonium chloride at a concentration of 0.01% for Ophthalmotrim-Dexamethasone and of 0.005% for Ophthalmotrim-Clobetasone as a preservative; the otic specialty has sodium nigapin (0.035%)—sodium nipasol (0.023%)-as the preservative.

In order to evaluate the preservative effectiveness the specifications of the British Pharmacopoeia 1988, European Pharmacopoeia 1992 A and Farmacopée Francaise 1989 for ophthalmic and topical products. The specialties tested have been contaminated with an inoculum of 1×10$^6$ c.f.u. of the microorganisms Pseudomonas aeruginosa ATCC 9027, Staphylococcus aureus ATCC 6538P, Candida albicans ATCC 10231 and Aspergillus niger ATCC 16404. The aliquots of the dilutions of the products have been grown on Tryptone agar-soybean and Sabouraud agar plates. The quantification of the microorganisms has been carried out at 0 and 6 hours, 1, 7, 14 and 28 days for the ophthalmic products and 0 hours and 2, 7, 14 and 28 days for the topical products.

The preservative benzalkonium chloride present in the specialties Ophthalmotrim-Dexamethasone and Ophthalmotrim-Clobetasone and sodium nigapin—sodium nipasol present in the specialty Otix-Dexamethasone comply with the specifications set forth in the British Pharmacpoeia 1988, European Pharmacopoeia 1992 A and Farmacopée Francaise 1989, for ophthalmic and topical products, respectively.

Effectiveness in vivo

The anti-infectious activity was determined in a model of bacterial keratitis caused by a strain of Pseudomonas aeruginosa coming from clinical isolation of an eye infection.

In order to evaluate the effectiveness of the association microbiological parameters were used carrying out the count of viable microorganisms in the homogenized ones from the cornea of treated animals and untreated animals. The results are expressed more clearly on the attached table where the great effectiveness of the clobetasone-ophthalmotrim association in the two types of evaluation is observed.

Test of antibacterial effectiveness in a model of keratitis in rabbits

Product: Ophthalmotrim-Clobetasone collyria    Protocol ref.: See ref. book Starting date: 27-07-92
Control: Ophthalm.-Clobetasone collyria vehic.    Book ref.: page 135 (Román-2) Ending date: 31-07-92
Reference: Ophthalmotrin collyria    Microorganism: P aeruginosa LC-30
                                     Dose by: Román-Assumpta Inoc. conc.: 6.8 × 10$^2$ cfu
Treatment: beginning immediately after inoculation, 50 μl of collyria at 7, 10, 13, 16 and 19 hours each day of the test

| Treatment | Clinical evaluation of the lesion (72 h.) n = 6 | | | | Microbiological evaluation (72 h.) n = 6 |
|---|---|---|---|---|---|
| | Ulcer | Extention | Opacity | x̄ Ind. Lesion ± s | x̄ log cfu ± s |
| control | 2.7 | 0.2 | 1.5 | 1.03 ± 0.73 | 4.43 ± 2.22 |
| Ophthalmotrim | 0.0 | 0.0 | 0.0 | 0.0 | 0.60 ± 1.47 |

| Test of antibacterial effectiveness in a model of keratitis in rabbits | | | | | |
|---|---|---|---|---|---|

Product: Ophthalmotrim-*Clobetasone collyria*  Protocol ref.: See ref. book Starting date: 27-07-92
Control: Ophthalm.-*Clobetasone collyria* vehic.  Book ref.: page 135 (Román-2) Ending date: 31-07-92
Reference: *Ophthalmotrin collyria*  Microorganism: *P aeruginosa* LC-30
Done by: Román-Assumpta Inoc. conc.: $6.8 \times 10^2$ cfu
Treatment: beginning immediately after inoculation, 50 μl of *collyria* at 7, 10, 13, 16 and 19 hours each day of the test

| | Clinical evaluation of the lesion (72 h.) n = 6 | | | | Microbiological evaluation (72 h.) n = 6) |
|---|---|---|---|---|---|
| Treatment | Ulcer | Extention | Opacity | x̄ Ind. Lesion ± s | x̄ log cfu ± s |
| Ophthalm.-Clobetasome | 0.0 | 0.0 | 0.0 | 0.0 | 0.65 ± 1.59 |

The anti-inflammatory effectiveness of Clobetasone butyrate associated with Trimethoprim and Polymyxin B sulfate has been tested in an experimental model of anterior uveitis in the eye of an albino rabbit. In this model 5 mcl of a bacterial endotoxin solution 0.1% (*Escheria coli* lipopolysaccharide) were injected by a needle with a caliber 33) into the stroma of the cornea.

The eye developed uveitis whose main signs were: thickening of the cornea (pachymetry), reddening and edema of the conjunctiva, appearance of a corneal arc, congestion of the iris and breaking the hemato-aqueous barrier of the eye with an increase of proteins (BioRad method) and polymorphonuclear leukocytes (count in a hemocytometer) in the aqueous humor. The quantification of the subjective parameters is done by means of observing the eye with a slit lamp. The follow-up of the inflammatory process is done 24 hours, 48 hours and 72 hours after the intrastromal injection.

Treatments are done by topical-ophthalmic instillation of isotonic solutions of the association of both coltyria of Cortophthal (Clobetasone butyrate) and Ophthalmotrim (Trimethoprim and Polymyxin B sulfate.) The experimental design determines the comparison of the effect of the association with that of the active principles (Clobetasone butyrate and trimethoprim-polymyxin B sulfate) thereof.

The experimental results found show that the clobetasone-trimethoprim-polymyxin association has an anti-inflammatory action on the uveitis markers that do not differ from that found for clobetasone and, in some cases, it manages to exceed it, just as is inferred from the following experimental data:

Pharmacology

TITLE: STUDY OF THE PHARMACOLOGICAL ACTION OF A COLLYRIA CONTAINING THE CLOBETASONE+TRIMETHOPRIM+POLYMYXIN ASSOCIATION IN AN EXPERIMENTAL MODEL OF UVEITIS IN THE EYE OF A RABBIT. IN COMPARISON WITH THE SPECIALTIES CORTOPTHAL (CLOBETASONE BUTYRATE COLLYRIA) AND OPHTHALMOTRIM (POLYMYXIN B SULFATE COLLYRIA).

TREATMENTS:

CLOBETASONE BUT.+TRIMETHOPRIM+POLYMYXIN SULF. batch 92281, vials 124, 125, 126 and 127

CORTOPHTHAL COLLYRIA (CLOBETASONE o.1%) batch G-2

OPHTHALMOTRIC COLLYRIA (TRIMETHOPRIM 0.1%+POLYMYXIN 10,000 u/ml) batch G-4

BRAUN SALINE SOLUTION (NaCl 0.9%) batch E-1931 CLINICAL EVALUATION AFTER 72 h (n=6)

| PROD | ERYT. | EDEM | SECR | IRIS | ARC | OPAC HA | COAG FIBRIN | PACHY. RED. % | CELLS/ mm3 |
|---|---|---|---|---|---|---|---|---|---|
| ASSOC. | 0,7 (0.5) | 0,3 (0,5) | 2,0 (0.0) | 0 | 0 | 0 | 0 | 98% | 1,5 |
| CLOB | 0,7 (0,5) | 0 | 1,5 (0,5) | 0 | 0 | 0 | 0 | 99% | 6 |
| OPHTHA | 1,5 (0.5) | 0,8 (0,4) | 1,8 (0,4) | 1,2 (0,8) | 0 | 0 | 0 | 71% | 112 |
| UNTREATED | 2,2 (0,8) | 1,5 (0,8) | 2,3 (0,5) | 2,2 (1) | 0,7 (2,6) | 0,8 (1) | 0,3 (0,5) | — | 1651 |

The results summarized in the above table correspond to the average obtained with six rabbits of each group.

The clobetasone—ophthalmotric (ASSOC.) gives some clinical values much lower than those of the untreated (UNTREATED) group. The pachymetric reduction values (PACHY. RED. %) (measurement of the thickness of the cornea) indicate that the association reduces the thickness of the untreated cornea. The measurement of the presence of cells in the aqueous humor (CELLS/mm$^3$) shows a number approximately one thousand times lower than in untreated animals. These results confirm the great anti-inflammatory effectiveness of the studied ophthalmotrim-anti-inflammatory drug association.

We claim:

1. Pharmaceutical formulation comprised of polymyxin, trimethoprim and an anti-inflammatory drug for ophthalmic and otic topical use, comprising 0.005–1.0% trimethoprim or pharmaceutically acceptable salts thereof;

0.001–5% of a steroidal or non-steroidal anti-inflammatory drug selected from the group consisting of dexamethasone, clobetasone, isomers thereof, esters thereof and pharmaceutically acceptable salts thereof; optionally, 0.7–1.4% of an isotonizing agent;

optionally, 0.01–2.0% of a pH buffer;
optionally, 0.01–2.0% of a viscosity modifying agent;
optionally, 0.1–2.0% of a wetting agent;
optionally, 0.01–2.0% of an antioxidant;
optionally, 0.001–1.0% of a preservative;
optionally, a vehicle suitable to the pharmaceutical form of the formulation said formulation having a pH between 4 and 8.5.

2. A formulation according to claim 1, characterized in that the polymyxin is polymyxin B or one of the pharmaceutically acceptable salts thereof.

3. A formulation according to claim 1, characterized in that the steroidal anti-inflammatory drug is medrisone, or an isomer, or an ester or one of the pharmaceutically acceptable salts thereof.

4. A formulation according to claim 1, characterized in that the steroidal anti-inflammatory drug is fluorometholone, or an isomer, or an ester or one of the pharmaceutically acceptable salts thereof.

5. A formulation according to claim 1, characterized in that the non-steroidal anti-inflammatory drug is diclofenac, or an isomer, or an ester or one of the pharmaceutically acceptable salts thereof.

6. A formulation according to claim 1, characterized in that the non-steroidal anti-inflammatory drug is indomethacin, or an isomer, or an ester or one of the pharmaceutically acceptable salts thereof.

7. A formulation according to claim 1, characterized in that the non-steroidal anti-inflammatory drug is flurbiprofen, or an isomer or an ester or one of the pharmaceutically acceptable salts thereof.

8. A formulation according to claim 1, characterized in that the non-steroidal anti-inflammatory drug is suprofen, an isomer, or an ester or one of the pharmaceutically acceptable salts thereof.

9. A formualtion according to claim 1, characterized in that the non-steroidal anti-inflammatory drug is pranoprofen, or an isomer, or an ester or one of the pharmaceutically acceptable salts thereof.

10. A formulation according to claim 1, characterized in that the non-steroidal anti-inflammatory drug is kerotolac, or an isomer, or an ester or one of the pharmaceutically acceptable salts thereof.

11. A formulation according to claim 1, characterized in that the isotonizing agent is selected from the group formed by sodium chloride, glycerol, mannitol and sorbitol.

12. A formulation according to claim 1, characterized in that the pH buffer is chosen from the group formed by citrates, borates and phosphates.

13. A formulation according to claim 1, characterized in that the viscosity modifying agent is chosen from the group formed by polyvinyl alcohol, polyvinylpyrrolidone, methylcellulose, hydroxypropylcellulose, hydroxyethylcellulose, carboxymethylcellulose and hydroxypropylmethylcellulose.

14. A formulation according to claim 1, characterized in that the wetting agent is chosen from the group formed by polyethoxylated fatty alcohols, polyethoxylated alkylphenols, polyethoxylated fatty acids, sorbitan esters and alkanolamides.

15. A formulation according to claim 1, characterized in that the chelating agent is chosen from the group formed by citric acid and disodium salt of ethylenediaminetetraacetic acid (EDTA.).

16. A formulation according to claim 1, characterized in that the antioxidant is chosen from the group formed by ascorbic acid and sodium methabisulfate.

17. A formulation according to claim 1, characterized in that the preservative is chosen from the group formed by quaternary ammonium derivatives such as benzalkonium chloride, cetylmethlammonium bromide, cetylpyridine chloride; organomercurial derivatives such as thimerosal, phenylmercuric acetate and phenylmercuric nitrate, and methyl and propyl p-hydroxybenzoates and sodium salts thereof, chlorbutanol, benzyl alcohol, chlorhexidine diacetate and digluconate.

18. A formulation according to claim 1, characterized in that the vehicle is chosen between solubility increasing agents such as cyclodextrins; cryoprotective agents such as dextrane, mannitol, citric acid, tartaric; a solvent such as ethanol, glycerol and propylenglycol; or a vehicle suitable for an ointment such as mineral oil, paraffin, lanolin or cholesterol.

19. A method of treating eye infection and inflammation comprising administering the formulation of claim 1.

20. A method of treating ear infection and inflammation comprising administering the formulation of claim 1.

* * * * *